(12) United States Patent
Chen et al.

(10) Patent No.: US 12,336,877 B2
(45) Date of Patent: Jun. 24, 2025

(54) ORAL TREATMENT DEVICE

(71) Applicant: Colgate-Palmolive Company, New York, NY (US)

(72) Inventors: Xiang Chen, Somerset, NJ (US); Suman Chopra, Monroe, NJ (US); Lin Fei, Kendall Park, NJ (US); Udayan Umapathi, Cambridge, MA (US)

(73) Assignee: Colgate-Palmolive Company, New York, NY (US)

( * ) Notice: Subject to any disclaimer, the term of this patent is extended or adjusted under 35 U.S.C. 154(b) by 531 days.

(21) Appl. No.: 17/778,736

(22) PCT Filed: Oct. 23, 2020

(86) PCT No.: PCT/US2020/070686
§ 371 (c)(1),
(2) Date: May 20, 2022

(87) PCT Pub. No.: WO2021/102455
PCT Pub. Date: May 27, 2021

(65) Prior Publication Data
US 2022/0409352 A1 Dec. 29, 2022

Related U.S. Application Data

(60) Provisional application No. 62/938,667, filed on Nov. 21, 2019.

(51) Int. Cl.
A61C 19/06 (2006.01)
A61C 5/62 (2017.01)
A61M 35/00 (2006.01)

(52) U.S. Cl.
CPC .............. A61C 19/063 (2013.01); A61C 5/62 (2017.02); A61M 35/006 (2013.01)

(58) Field of Classification Search
CPC ....... A61C 19/063; A61C 5/62; A61C 19/066; A61C 19/001; A61C 19/06; A61M 25/006
(Continued)

(56) References Cited

U.S. PATENT DOCUMENTS 4,863,380 A 9/1989 Creed
4,925,327 A * 5/1990 Wirt ...................... B65D 47/42
604/3
(Continued)

FOREIGN PATENT DOCUMENTS

CN 107278144 A 10/2017
CN 108135685 A 6/2018
(Continued)

OTHER PUBLICATIONS

International Search Report and the Written Opinion of the International Searching Authority issued in International Application PCT/US2020/070686 mailed Dec. 21, 2020.

Primary Examiner — David J Walczak

(57) ABSTRACT

An oral treatment device for dispensing an oral treatment composition onto a user's teeth. The oral treatment device may include a storage and delivery component and an applicator component. The storage and delivery component may include a body having a reservoir, a frangible capsule containing the oral treatment composition located in the reservoir, and a delivery member. The applicator component may include a pad portion formed of a liquid absorbing material. The applicator component may be alterable between an attached state whereby the delivery member is fluidly coupled to the pad portion and a detached state whereby the applicator component is detached from the storage and delivery component and can be placed into contact with the user's teeth. The frangible capsule may be in a sealed state until broken by a user at which point the oral (Continued)

treatment composition may flow into the pad portion of the applicator component.

19 Claims, 6 Drawing Sheets

(58) Field of Classification Search
USPC .................................................. 401/132–135
See application file for complete search history.

(56) References Cited

U.S. PATENT DOCUMENTS

| | | | |
|---|---|---|---|
| 5,098,297 A | 3/1992 | Chari et al. | |
| 5,490,736 A * | 2/1996 | Haber | A61M 35/006 |
| | | | 604/3 |
| 6,099,307 A | 8/2000 | Discko, Jr. | |
| 6,726,482 B2 | 4/2004 | Atkins et al. | |
| 6,902,335 B2 | 6/2005 | Bergey et al. | |
| 7,044,671 B2 | 5/2006 | Parikh et al. | |
| 7,198,623 B2 | 4/2007 | Fischer et al. | |
| 7,963,712 B2 | 6/2011 | Sogaro | |
| 8,459,892 B2 | 6/2013 | Hohlbein et al. | |
| 9,138,046 B2 | 9/2015 | Jimenez et al. | |
| 9,237,798 B2 | 1/2016 | Jimenez et al. | |
| 9,554,641 B2 | 1/2017 | Worthington et al. | |
| 9,717,892 B2 | 8/2017 | Kaufman et al. | |
| 10,092,086 B2 | 10/2018 | Gatzemeyer et al. | |
| 2006/0072958 A1* | 4/2006 | Tsaur | A61C 19/063 |
| | | | 604/3 |
| 2007/0231051 A1* | 10/2007 | Flores | A61P 31/02 |
| | | | 401/132 |
| 2008/0274066 A1 | 11/2008 | Montgomery | |
| 2012/0251981 A1 | 10/2012 | Piergallini et al. | |
| 2014/0133895 A1* | 5/2014 | Dockery | A45D 29/007 |
| | | | 401/196 |

FOREIGN PATENT DOCUMENTS

| | | |
|---|---|---|
| WO | 1999/005987 | 2/1999 |
| WO | 2005/011582 | 2/2005 |
| WO | 2006/071300 | 7/2006 |
| WO | 2008/072189 | 6/2008 |
| WO | 2009/132223 | 10/2009 |
| WO | 2016/123110 | 8/2016 |
| WO | WO2016137617 A1 | 9/2016 |
| WO | 2017/061980 | 4/2017 |
| WO | 2021/0102455 | 5/2021 |

* cited by examiner

ORAL TREATMENT DEVICE

BACKGROUND

Toothpaste and mouth rinse are common oral hygiene products that are used daily, but they typically only stay inside of a user's mouth for very short periods of time and are rinsed off once brushing or swooshing is done. Formulators have made attempts to develop toothpastes and mouth rinses such that the active ingredients therein will stay inside the mouth longer. However, that effort can be easily compromised if users shorten the brushing or rinsing time. Moreover, toothbrushing and mouth rinsing typically only takes place in a home environment because people do not tend to take toothbrushes, tubes of toothpaste, and mouth rinses with them as part of their daily activities. There is a need for devices and methods for conveniently cleaning and otherwise treating teeth in a convenient and discrete manner so that the active ingredients stay in the mouth for a longer period of time.

BRIEF SUMMARY

The present invention is directed to an oral treatment device for dispensing an oral treatment composition onto a user's teeth. The oral treatment device may include a storage and delivery component and an applicator component. The storage and delivery component may include a body having a reservoir, a frangible capsule containing the oral treatment composition located in the reservoir, and a delivery member. The applicator component may include a pad portion formed of a liquid absorbing material. The applicator component may be alterable between an attached state whereby the delivery member is fluidly coupled to the pad portion and a detached state whereby the applicator component is detached from the storage and delivery component and can be placed into contact with the user's teeth. The frangible capsule may be in a sealed state until broken by a user at which point the oral treatment composition may flow into the pad portion of the applicator component.

In one aspect, the invention may be an oral treatment device comprising: a storage and delivery component comprising: a body comprising a reservoir; an oral treatment composition in the reservoir; at least one delivery member extending from a first end to a second end, the first end being fluidly coupled to the reservoir; and a frangible barrier separating the oral treatment composition from the first end of delivery member; an applicator component comprising a pad portion formed of a liquid absorbing material, the applicator component alterable between: (1) an attached state whereby the second end of the delivery member is fluidly coupled to the pad portion; and (2) a detached state whereby the applicator component is detached from the storage and delivery component for application to a user's teeth; and wherein application of a force on the reservoir ruptures the frangible barrier to enable the oral treatment composition to flow through the at least one delivery member to the pad portion of the applicator component.

In another aspect, the invention may be an oral treatment device comprising: a storage and delivery component comprising: a body comprising a reservoir; an oral treatment composition in the reservoir; a capillary member extending from a first end to a second end, the first end being fluidly coupled to the reservoir; and a frangible barrier separating the oral treatment composition from the first end of the capillary member; and an applicator component comprising a pad portion formed of a liquid absorbing material, the applicator component alterable between: (1) an attached state whereby the second end of the capillary member is in contact with the pad portion; and (2) a detached state whereby the applicator component is detached from the storage and delivery component for application to a user's teeth; and wherein the frangible barrier is alterable from a sealed state to an unsealed state, and wherein in the unsealed state the oral treatment composition flows from the reservoir to the pad portion of the applicator component through the capillary member due to capillary action.

In yet another aspect, the invention may be an oral treatment device comprising: a storage and delivery component comprising: a body comprising a reservoir; an oral treatment composition in the reservoir; a capillary member extending from a first end to a second end, the first end being fluidly coupled to the reservoir; and a frangible barrier separating the oral treatment composition from the first end of the capillary member; and an applicator component comprising a pad portion formed of a liquid absorbing material, the second end of the capillary member in contact with the pad portion of the applicator component; and wherein upon rupture of the frangible barrier, the oral treatment composition flows from the reservoir to the pad portion of the applicator component through the capillary member due to capillary action.

In still another aspect, the invention may be a method of treating teeth comprising: rupturing a barrier that is located within a reservoir of a storage and delivery component of an oral treatment device to enable an oral treatment composition to flow, via capillary action through a capillary tube of the storage and delivery component, from the reservoir to a liquid absorbing material of an applicator component that is coupled to the storage and delivery component; detaching the applicator component from the storage and delivery component; and placing the liquid absorbing material of the applicator in contact with one or more teeth to dispense the oral treatment composition onto the one or more teeth.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
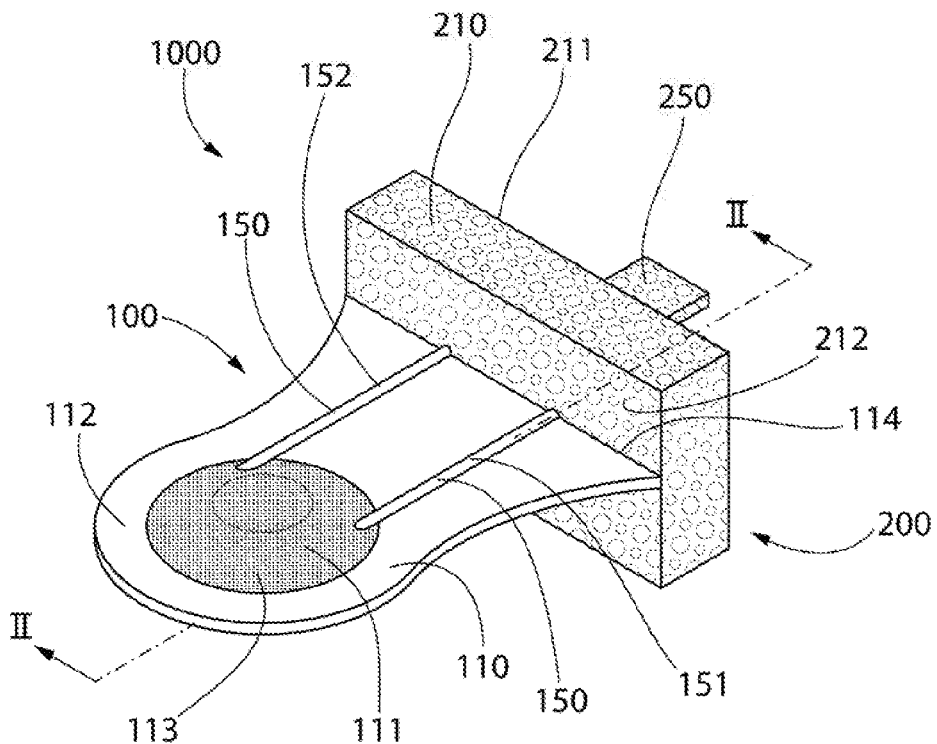
FIG. 1 is a perspective view of an oral treatment device in accordance with a first embodiment of the present invention, the oral treatment device including a storage and delivery component and an applicator component in an attached state.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 2:
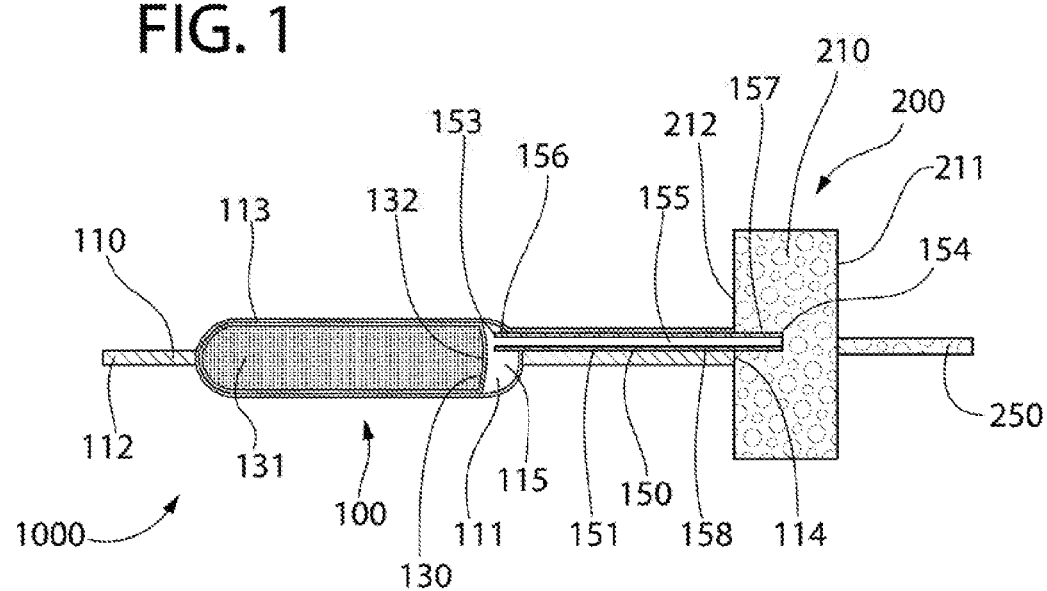
FIG. 2 is a cross-sectional view taken along line II-II of FIG. 1.

Referring first to FIGS. 1 and 2, an oral treatment device 1000 is illustrated in accordance with an embodiment of the present invention. The oral treatment device 1000 generally comprises a storage and delivery component 100 and an applicator component 200 that are detachably coupled together. Thus, prior to use for treating teeth, the applicator component 200 may be coupled to the storage and delivery component 100. During use for treating teeth, the applicator component 200 may be detached from the storage and delivery component 100 so that it can be placed within a user's oral cavity and put into contact with facial surfaces of the user's teeth (or any other region within the oral cavity) for treatment thereof. Prior to detachment of the applicator component 200 from the storage and delivery component 100, an oral treatment composition (or an active agent) is made to flow from the storage and delivery component 100 where it is stored prior to use into the applicator component 200 where it can be dispensed onto the user's teeth.

The storage and delivery component 100 generally comprises a body 110 comprising a reservoir 111, a frangible capsule 130 containing an oral treatment composition 131, and at least one delivery member 150. Each of these parts of the storage and delivery component 100 will be described in turn below. Generally, however, it should be appreciated that the storage and delivery component 100 holds or otherwise stores the oral treatment composition until it is ready for use. Thus, the oral treatment composition remains stored within the storage and delivery component 100 until the moment a user decides to use the oral treatment device 1000, at which point the oral treatment composition is permitted or forced to flow to the applicator component 200 as described herein.

In the exemplified embodiment, the body 110 comprises a first portion 112 and a second portion 113. The first portion 112 is a plate-like member that may be formed from a rigid material such as a hard plastic in some embodiments. The second portion 113 may be formed of a resilient material and may define the reservoir 111 of the body 110. The resilient material of the second portion 113 may be an elastomeric material, a thermoplastic elastomer, rubber, or any other material that is capable of flexing or being compressed and/or stretched during normal use. It may be possible in other embodiments for the second portion 113 to be formed from a thin plastic material which is bendable or squeezable by a user. In any event, the second portion 113 of the body 110 should be squeezable, compressible, or the like to compress the reservoir 111 for purposes of dispensing the oral treatment composition 131 as described herein.

In the exemplified embodiment, the second portion 113 fully forms the reservoir 111 such that the second portion 113 defines, by itself, a cavity that forms the reservoir 111. Thus, in the exemplified embodiment the more resilient material of the second portion 113 defines the entirety of the reservoir 111. However, the invention is not to be so limited in all embodiments and in some alternative embodiments the second portion 113 and the first portion 112 could collectively define the reservoir 111. For example, the first portion 112 could define a floor of the reservoir 111 with the second portion 113 forming a sidewall and top boundary of the reservoir 111 (i.e., the second portion 113 could be a dome-shaped portion that is coupled to the first portion 112). Thus, variations from that which is depicted in the drawings are possible within the scope of the invention described herein.

The body 110 has a specific shape in the exemplified embodiment, but it is not in any way intended to be so limited. Specifically, in the exemplified embodiment the body 110 has a rounded section and an outwardly tapering section extending from the rounded section. The rounded section comprises the reservoir 111 and the delivery member 150 is located along the outwardly tapering section. However, in other embodiments the body 110 could be square, triangular, circular, or the like. In the exemplified embodiment, the body 110 comprises an end surface 114, which is the terminal end of the outwardly tapering section. In the exemplified embodiment, the end surface 114 is a flat edge of the body 110 and the applicator component 200 is positioned adjacent to this end surface 114 when the applicator component 200 is attached to the storage and delivery component 100 as shown in FIGS. 1 and 2.

The frangible capsule 130 is positioned within the reservoir 111 of the body 110, as best seen in FIG. 2. Specifically, in the exemplified embodiment the frangible capsule 130 is fully enclosed within the reservoir 111 such that no portion of the frangible capsule 130 is exposed. The frangible capsule 130 fully retains the oral treatment composition 131 therein when it is in a sealed state as shown in FIG. 2. The frangible capsule 130 can be altered to an unsealed state as discussed further below, which results in the oral treatment composition 131 flowing out of the frangible capsule 130 and into the reservoir 111.

In the exemplified embodiment, the frangible capsule 130 may be made from any material such that the frangible capsule 130 remains sealed until a force or pressure is acted upon it which causes the frangible capsule 130 to break open. Specifically, a sufficient amount of force or pressure on the frangible capsule 130 will cause a frangible seal 132 of the frangible capsule 130 to break so that the oral treatment composition 131 can flow out therefrom. In the exemplified embodiment, the frangible seal 132 is located at an end thereof, but it could be located at any other position along the frangible capsule 130 so long as adequate pressure applied to the frangible capsule 130 will cause the frangible seal 132 to break. Thus, the frangible seal 132 could be located at the opposite end of the frangible capsule 130 or at any position therealong that is between the ends of the frangible capsule 130. The frangible seal 132 may be a pre-weakened region of the frangible capsule 130, an area at which the frangible capsule 130 is bonded to form an enclosed structure (such as by an adhesive, welding, or the like process), or a part of the frangible capsule 130 that is formed of a weaker material than the rest so that pressure causes the frangible seal 132 to break as described herein. The frangible capsule 130 may be formed from plastic, synthetic plastic, glass, rubber, elastomers, or the like, or combinations thereof, in various embodiments.

As noted above, the frangible capsule 130 contains the oral treatment composition 131, which may also be referred to herein as an active agent (or the oral treatment composition 131 may comprise an active agent). In the exemplified embodiment, the oral treatment composition 131 is a low viscous liquid to permit its flow to the applicator component 200 via capillary action as described herein below. The oral treatment composition 131 may be any composition desired to treat various ailments that affect the teeth and oral cavity and/or a composition that enhances the appearance of a user's teeth. For example, the oral treatment composition 131 may be a tooth whitening composition (such as a peroxide containing tooth whitening composition), an enamel strengthening composition, an anti-sensitivity composition, a gum soothing or healing composition, a breath freshening composition, or the like. Other contemplated oral treatment compositions 131 include, for example without limitation, antibacterial agents; oxidative or whitening agents; enamel strengthening or repair agents; tooth erosion preventing agents; tooth sensitivity ingredients; gum health actives; nutritional ingredients; tartar control or anti-stain ingredients; enzymes; sensate ingredients; flavors or flavor ingredients; breath freshening ingredients; oral malodor reducing agents; anti-attachment agents or sealants; diagnostic solutions; occluding agents, dry mouth relief ingredients; catalysts to enhance the activity of any of these agents; colorants or aesthetic ingredients; and combinations thereof. Any agent that could potentially provide a benefit to a user's teeth and/or other oral cavity surfaces could form the oral treatment composition.

The frangible capsule 130 is alterable between a sealed state (FIG. 2) and an unsealed state (FIG. 4), and the manner in which this is achieved will be described in more detail below with reference to FIGS. 3 and 4. However, it should be appreciated that in the sealed state the oral treatment composition 131 is located entirely within the frangible capsule 130 and in the unsealed state the oral treatment capsule 131 flows out of the frangible capsule 130 and into the reservoir 111, from the reservoir 111 into the delivery member 150, and through the delivery member 150 into the applicator component 200. This flow of the oral treatment composition 131 will be described in more detail below with reference to FIGS. 3 and 4. In the sealed state, the frangible capsule 130 is a sealed capsule so that the oral treatment composition 131 stored therein cannot leak out. It is only when the frangible capsule 130 or seal thereof is broken that the oral treatment material 131 can flow to the applicator component 200.

As seen in FIG. 2, the frangible capsule 130 has a size and/or volume that is less than the size and/or volume of the reservoir 111. Thus, when the frangible capsule 130 is positioned within the reservoir 111 of the body 110, there is an air gap 115 that remains in the reservoir 111. Specifically, the air gap 115 is a portion of the reservoir 111 that is free of the frangible capsule 130 and the oral treatment composition 131 when the frangible capsule is in the sealed state depicted in FIG. 2. Stated another way, in the exemplified embodiment the frangible capsule 130 does not take up the entire volume of the reservoir 111 when it is in the sealed state. In other embodiments, the frangible capsule 130 could take up the entire volume of the reservoir 111, but this would require an adjustment to the positioning of the delivery member 150. Moreover, it might be possible in some embodiments to omit the frangible capsule 130 and to store the oral treatment composition 131 directly in the reservoir 111. In such embodiments, the reservoir 111 itself would have a frangible or breakable seal to prevent and permit flow of the oral treatment composition 131 to the applicator component 200.

Finally, the storage and delivery component 100 comprises the delivery member 150, which is the portion of the storage and delivery component 100 that carries the oral treatment composition to the applicator component 200. In some embodiments, the delivery member 150 may be a capillary member such that it can carry the oral treatment composition from the reservoir 111 to the applicator component 200 via capillary action. In the exemplified embodiment, there are two of the delivery members 150. However, in other embodiments there may be just one of the delivery members 150 whereas in other embodiments there may be more than two of the delivery members 150. The more delivery members there are, the quicker the oral treatment composition 131 can be moved from the reservoir 111 to the applicator component 200 once the frangible capsule 130 is ruptured or otherwise broken.

In the exemplified embodiment, the delivery member(s) 150 comprises a first tube 151 and a second tube 152 (as noted, there are two delivery members 150, so one of the delivery members 150 comprises the first tube 151 and the other of the delivery members 150 comprises the second tube 152). The first and second tubes 151, 152 may be considered first and second delivery members in some embodiments. In embodiments whereby the delivery member 150 is intended to carry the oral treatment composition 131 from the reservoir 111 to the applicator component 200 by capillary action, the first and second tubes 151, 152 may have a cross-sectional area that is configured to force the oral treatment composition 131 to flow therethrough by capillary action upon the frangible capsule 130 being altered from the sealed state to an unsealed state. Fluids, such as the oral treatment composition 131, may flow via capillary action by the combination of surface tension (which is caused by cohesion within the fluid) and adhesive forces between the fluid and the inner wall of the first and second tubes 151, 152 to propel the fluid. Thus, if the cross-sectional area of the first and second tubes 151, 152, and more particularly the passageway thereof, is sufficiently small and the oral treatment composition 150 has a sufficient cohesion, the oral treatment composition 150 will be able to flow passively without user assistance and without gravity, from the reservoir 111 to the applicator component 200.

In one alternative embodiment, the delivery member 150 may be formed out of a porous material to achieve capillary action flow of the oral treatment composition 150. Such porous material may be a foam material, a cellulosic or paper-based material, a ceramic material, or the like. In still other embodiments, capillary action flow is not required and a user may squeeze the reservoir 111 until a sufficient amount of the oral treatment composition 131 has moved from the reservoir 111 to the applicator component 200. However, capillary action flow may be desirable in some embodiments because it enables a user to take care of other needs while waiting for the oral treatment composition 131 to flow passively from the reservoir 111 to the applicator component 200.

Referring to the exemplified embodiment, the first tube 151 will be described in greater detail. It should be appreciated that the second tube 152 has an identical construction and thus the description of the first tube 151 is equally applicable to the second tube 152 despite there being no disclosure directed specifically to the second tube 152. Furthermore, in some embodiments there may be only one deliver member 150, or one tube 151, such that the second tube 152 could be omitted.

The first tube 151 comprises a first end 153 and a second end 154. There are openings in the first and second ends 153, 154 and a passageway 155 extending between the first and second ends 153, 154. A first portion 156 of the first tube 151 that comprises the first end 153 protrudes into and is located within the reservoir 111, and more specifically within the air gap 115 of the reservoir 111. Thus, the first end 153 of the first tube 151 is open to and fluidly coupled to the oral treatment composition 111 once it is dispersed from the frangible capsule 130. A second portion 157 of the first tube 151 that comprises the second end 154 protrudes from the end surface 114 of the body 110 of the storage and delivery component 100. Furthermore, the second portion 157 of the first tube 151 is fluidly coupled to the applicator component 200. The details of the fluid coupling between the first tube 151 and the applicator component 200 will be described in greater detail below.

A third portion 158 of the first tube 151 that is between the first and second portions 156, 157 is positioned along the body 110 of the storage and delivery component 100. The third portion 158 of the first tube 151 does not include either of the first or second ends 153, 154 of the first tube 151. In the exemplified embodiment, the third portion 158 of the first tube 151 is sandwiched between the first portion 112 and the second portion 113 of the body 110. In other embodiments, the third portion 158 of the first tube 151 may be embedded solely within the first portion 112 of the body 110 or solely within the second portion 113 of the body 110. Thus, in the exemplified embodiment no part of the third portion 158 of the first tube 151 is exposed. By embedding the third portion 158 of the first tube 151 within the body 110, the first tube 151 is effectively coupled to the body 110. This ensures that the first tube 151 remains in place with the first end 153 located in the reservoir 111 and the second end 154 fluidly coupled to the applicator component 200.

Of course, in some alternative embodiments portions of the third portion 158 of the first tube 151 may be exposed and not embedded within the body 110. For example, the second portion 113 of the body 110 may cover a part of the third portion 158 of the first tube 151, but not the entirety of it. Alternatively, the third portion 158 of the first tube 151 may be coupled to the body 110 in other ways, such as using adhesives, welding, staples, fasteners, or the like. In such embodiments, the third portion 158 of the first tube 151 may be exposed entirely along its length. In some embodiments, the mere fact that the first portion 156 of the first tube 151 is located within the reservoir 111 may be sufficient to couple the first tube 151 (i.e., delivery member 150) to the body 110. Regardless of how it is achieved, the delivery member 150 (i.e., the first tube 151 and/or the second tube 152) should be coupled to the body 110 to form the storage and delivery component 100 of the oral treatment device 1000.

Still referring to FIGS. 1 and 2, in this embodiment the applicator component 200 comprises a pad portion 210 and a bite tab 250. The pad portion 210 of the applicator component 200 is preferably formed of a liquid absorbing material, which may include porous materials, foam materials including soft and/or hard foams, fibrous materials, ceramics, sponge-like materials, cotton, activated carbon, or the like. Regardless of the specific material used, the pad portion 210 should be pliable in some embodiments so that it can be flexed to conform to facial surfaces of the user's teeth, which are collectively arcuate. In the exemplified embodiment, the major surfaces of the pad portion 210 are flat or planar, and thus such flexing thereof is desirable to ensure conformance to the user's teeth during use. In other embodiments, the pad portion 210 or at least a surface thereof that is intended to contact the user's teeth may be arcuate in an unbiased state so that flexing or bending of the pad portion 210 is not needed to conform to the teeth surfaces.

In the exemplified embodiment, the pad portion 210 of the applicator component 200 comprises a front surface 211 and a rear surface 212 opposite the front surface 211. The pad portion 210 may be formed entirely of the capillary material so that it can soak up a liquid such as the oral treatment composition 131 as described herein. In the exemplified embodiment, the pad portion 210 of the applicator component 200 is placed adjacent to the end surface 114 of the body 110 of the storage and delivery component 100 without being physically coupled to the body 110. More specifically, in the exemplified embodiment the rear surface 212 of the pad portion 210 is in abutment with the end surface 114 of the body 110. Although the applicator component 200 is not physically coupled to the body 110, the applicator component 200 is physically coupled to the delivery member 150, which thereby couples the applicator component 200 to the storage and delivery component 100. Of course, in other embodiments the applicator component 200 may be physically detachably coupled to the body 110 as an alternative to or in addition to its coupling to the delivery member 150, one example of which will be described with reference to FIGS. 9 and 10.

In the exemplified embodiment, the second portion 157 of the first tube 151 of the delivery member 150 which protrudes from the end surface 114 of the body 110 of the storage and delivery component 100 is embedded within the pad portion 210 of the applicator component 200 between the front and rear surfaces 211, 212 of the pad portion 210. Thus, the second end 154 of the first tube 151 is located between the front and rear surfaces 211, 212 of the pad portion 210 of the applicator component 200. The invention is not to be so limited in all embodiments. Specifically, in other embodiments the second end 154 of the first tube 151 need only be fluidly coupled to the pad portion 210 of the applicator component 200 so that the oral treatment composition 131 can flow through the first tube 151 to the pad portion 210 of the applicator component 200. Thus, the second end 154 of the first tube 151 may be pressed against the rear surface 212 (or any other exterior surface) of the pad portion 210 of the applicator component 200 in some embodiments rather than having it be embedded within the pad portion 210.

In the exemplified embodiment the embedding of the second portion 157 of the first tube 151 into the pad portion 210 of the applicator component 200 is what detachably couples the applicator component 200 to the storage and delivery component 100. Thus, in embodiments where the second portion 157 of the first tube 151 is not embedded within the pad portion 210 of the applicator component 200, other structures may be included to achieve the detachable coupling between the applicator component 200 and the storage and delivery component 100. One such embodiment will be described with reference to FIGS. 9 and 10. FIGS. 1 and 2 illustrate the applicator component 200 in an attached state, which is what has been described herein above, whereby the second end 154 of the first tube 151 of the delivery member 150 is fluidly coupled to the pad portion 210 of the applicator component 200. The applicator component 200 can be altered from the attached state to a detached state whereby the applicator component 200 is detached and separated from the storage and delivery component 100, which will be described with reference to FIG. 7.

The bite tab 250 of the applicator component 200 protrudes from the front surface 211 of the pad portion 210 of the applicator component 200. In the exemplified embodiment, the bite tab 250 is formed integrally with the pad portion 210 out of the liquid absorbing material. However, the invention is not to be so limited in all embodiments and the bite tab 250 could be a rigid material such as plastic, metal, or the like embedded within and protruding from the front surface 211 of the pad portion 210.

The bite tab 250 is a flat member that extends from the front surface 211 of the pad portion 210 such that it can be clenched between the occlusal surfaces of the upper and lower teeth. In the exemplified embodiment, the bite tab 250 is a singular structure protruding from the front surface 211 of the pad portion 210. In other embodiments the bite tab 250 may comprise a plurality of structures protruding from the front surface 211 of the pad portion 210 in a spaced apart manner. In the exemplified embodiment, when the applicator component 200 is in use to dispense the oral treatment composition 131 onto the teeth, the bite tab 250 is bit to hold the applicator component 200 in place. Of course, the invention is not to be so limited in all embodiments. In some alternative embodiments, the bite tab 250 may be omitted. In such embodiments, the applicator component 200 may be held in place by being disposed between the user's inner lip and facial surfaces of the teeth. In still other embodiments, the applicator component 200 may comprise a liquid activated adhesive coating on the front surface 211 of the pad portion 210. In such an embodiment, when the oral treatment composition 131 is absorbed by the pad portion 210 of the applicator component 200, it will activate the liquid activated adhesive coating to make it adhesive. As a result, when the applicator component 200 is placed in the oral cavity, the adhesive coating will cause it to adhere to the user's teeth during use. A user could also wet the front surface 211 of the pad portion 210 of the applicator component 200 to activate the liquid activated adhesive coating.

In still other embodiments, the pad portion 210 of the applicator component 200 could be coated with certain waterproof compositions on one or more of its outside surfaces. However, in such embodiments it may be preferable to leave the front surface 211 of the pad portion 210 which is configured to be in contact with the facial surfaces of the teeth during use uncoated in order to allow the active agent of the oral treatment composition 131 to be released from the front surface 211. This may be desirable in certain situations dependent upon the material of the oral treatment composition 131. For example, if the oral treatment composition 131 is a fluoride for cavity prevention that is intended for use only on the enamel, it may be desirable to coat every surface of the pad portion 210 other than the front surface 211 with a waterproof composition so that the oral treatment composition 131 is only dispensed from the front surface 211. Similarly, if the oral treatment composition 131 is a bleaching agent for teeth whitening, such agent may irritate or cause pain to the gums of some people. Thus, coating the outer surfaces of the pad portion 210 other than the front surface 211 with a waterproof material or composition may prevent the bleaching agent from contacting the gums and/or inner surfaces of the lips in a significant way, which may prevent such irritation or pain.

The pad portion 210 of the applicator component 200 may have any of a variety of different sizes. For example, in one embodiment the pad portion 210 may be configured to contact the facial surfaces of either the upper or lower teeth, but not both. In other embodiments, the pad portion 210 may be configured to contact the facial surfaces of the upper and lower teeth simultaneously. Thus, the size of the pad portion 210 of the applicator component 200 may be adjusted accordingly depending on desired end use.

Having described the structure of the oral treatment device 1000, its function and use will now be described with reference to FIGS. 3-8B. Referring to FIGS. 3 and 4, the oral treatment device 1000 is illustrated with a force F being applied onto an exterior of the body 110 that defines the reservoir 111. Upon applying a sufficient force F onto the body 110 as shown, the frangible seal 132 of the frangible capsule 130 will break or rupture, thereby allowing the oral treatment composition 131 to flow out of the confines of the frangible capsule 130 and into the location that was previously the air gap 115 of the reservoir 111. Upon breaking the frangible capsule 130, the oral treatment composition 131 will immediately flow to fill in the spaces of the reservoir 111 that were previously empty.

In some embodiments, once the frangible capsule 130 is broken or ruptured, a user can release the force F and the oral treatment composition 131 will nonetheless continue on its flow path towards the applicator component 200. Specifically, in some embodiments, even without the continued application of the force F, once the frangible capsule 130 is ruptured, the oral treatment composition 131 will flow into and through the first and second tubes 151, 152 (i.e., the delivery member 150) until it gets absorbed by the liquid absorbing material of the pad portion 210 of the applicator component 200. In such embodiments, the flow of the oral treatment composition 131 from the reservoir 111 to the applicator component 200 is achieved by capillary action, which, as described above, is a passive flow that can be achieved by the combination of surface tension of the oral treatment composition 131 and adhesive forces between the oral treatment composition 131 and the inner wall of the first and/or second tubes 151, 152 (i.e., the delivery member 150). In other embodiments, a user may continue to apply the force F (or a lesser or greater force) onto the body 110 or the reservoir 111 to force the flow of the oral treatment composition 131 through the delivery member 150 to the applicator component 200.

Figure 3:
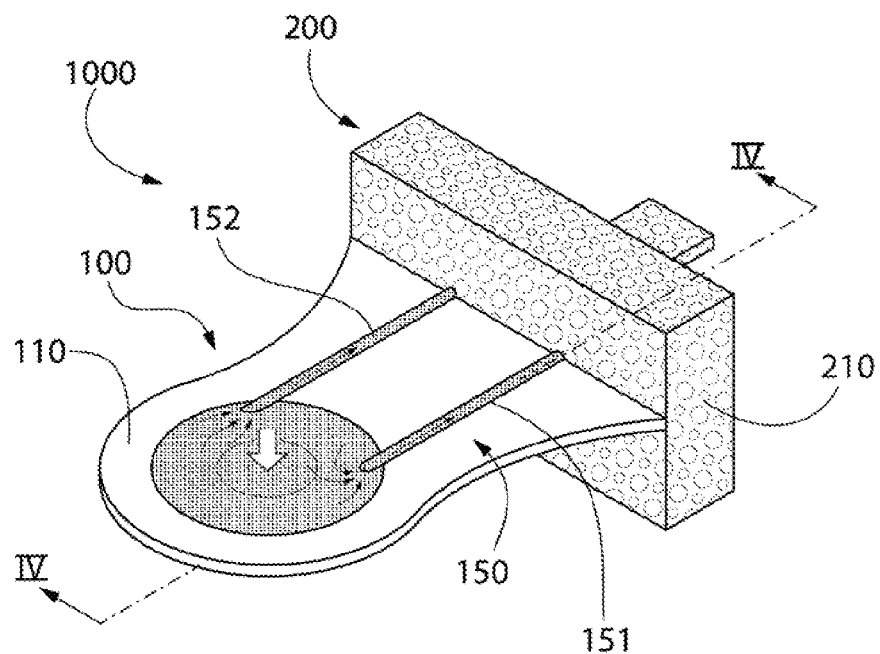
FIG. 3 is a perspective view of the oral treatment device of FIG. 1, wherein a force or pressure is being applied to a reservoir of the storage and delivery component to release an oral treatment composition from a frangible capsule located in the reservoir.
Figure 4:
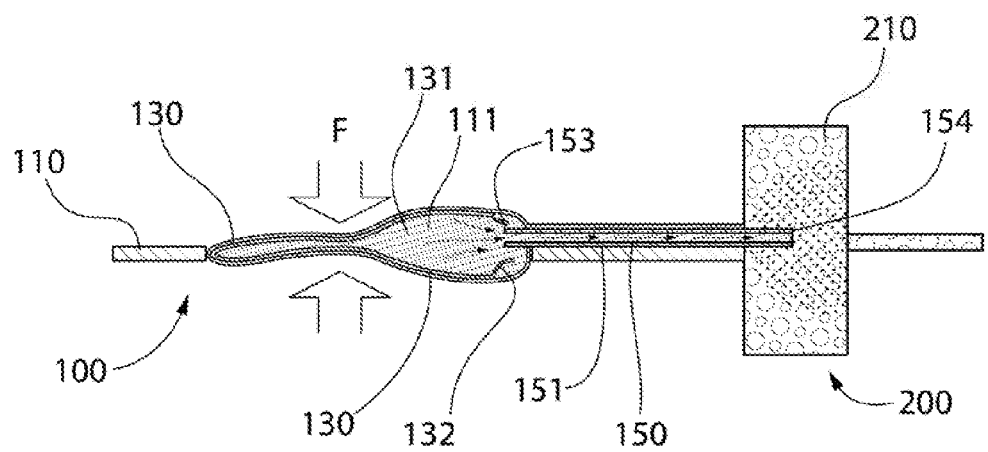
FIG. 4 is a cross-sectional view taken along line IV-IV of FIG. 3.

As shown in FIGS. 3 and 4, the frangible capsule 130 has broken or ruptured and the oral treatment composition 131 flows through the first tube 151 (i.e., the delivery member 150) and into the liquid absorbing material of the pad portion 210 of the applicator component 200.

Although described herein as being a frangible capsule 130, the invention is not to be so limited in all embodiments. In some embodiments, there may be a frangible barrier that, when intact, separates the oral treatment composition 131 in the reservoir 111 from the first end 153 of the delivery member 150. Upon rupture of the frangible barrier, the oral treatment composition 131 in the reservoir 111 may be able to flow freely to the first end 153 of the delivery member 150. Thus, rather than having a separate capsule located in the reservoir 111 that holds the oral treatment composition 131, the oral treatment composition 131 may simply be in the reservoir 111, and a frangible barrier prevents the oral treatment composition 131 from being fluidly coupled to the delivery member 150. Stated another way, the reservoir 111 may be divided into a first portion and a second portion by the frangible barrier. In such an embodiment, the first portion of the reservoir 111 contains the oral treatment composition 131 and the second portion (i.e., the air gap 115) of the reservoir 111 does not contain any of the oral treatment composition 131 so long as the frangible barrier is intact and not ruptured (i.e., sealed). Upon rupture of the frangible barrier, the oral treatment composition 131 flows into the second portion (i.e., the air gap 115) of the reservoir and then into the delivery member 150.

Figure 5:
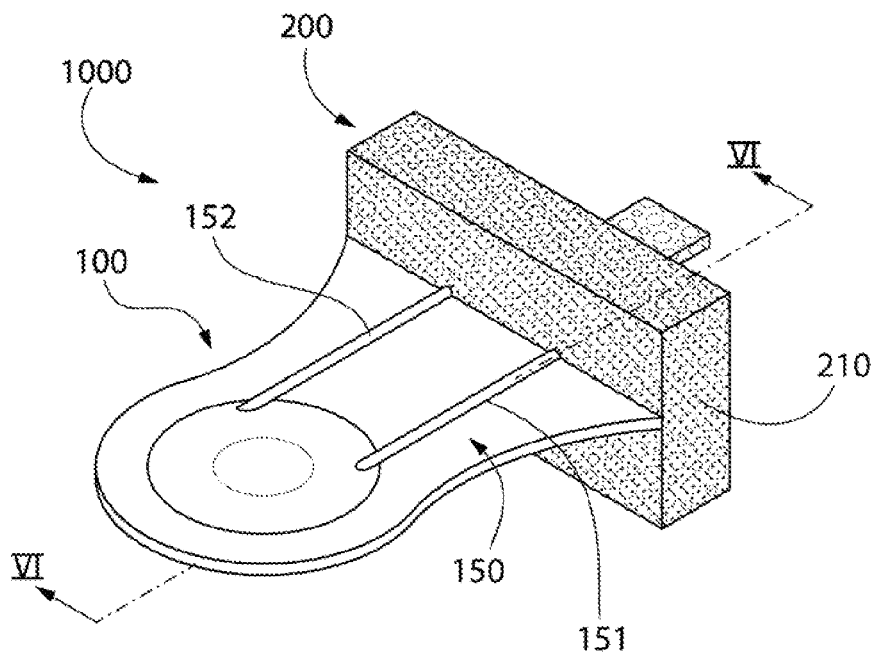
FIG. 5 is a perspective view of the oral treatment device of FIG. 1, wherein the oral treatment composition has traveled from the reservoir to the applicator component.
Figure 6:
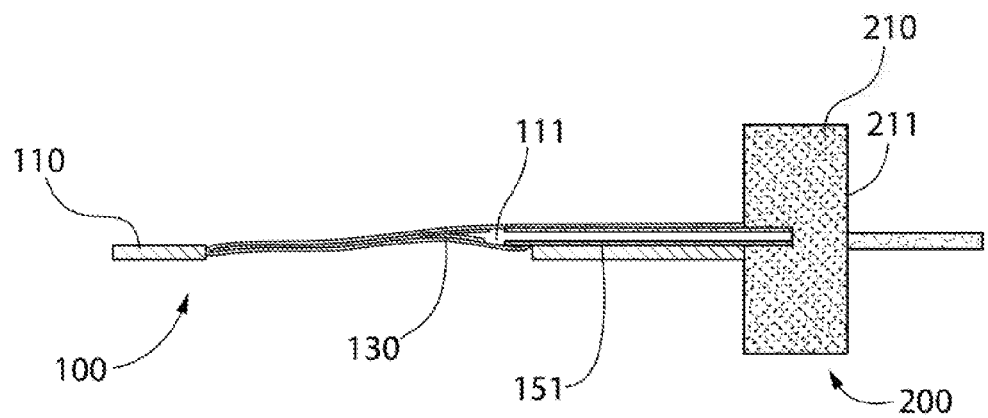
FIG. 6 is a cross-sectional view taken along line VI-VI of FIG. 5.

Referring to FIGS. 5 and 6, the oral treatment composition 131 has been depleted from the reservoir 111 of the body 110 of the storage and delivery component 100. Thus, the entire contents of the frangible capsule 130, meaning all of the oral treatment composition 131 that was previously contained therein, has moved to and been absorbed by the liquid absorbing material of the pad portion 210 of the applicator component 200. This can be achieved by passive capillary action, squeezing action by a user, or a combination of the two in various embodiments. Regardless, once the oral treatment composition 131 has been absorbed by the pad portion 210 of the applicator component 200, the applicator component 200 is ready for use to treat a user's teeth or other oral cavity surfaces. Of course, it should be appreciated that in some embodiments a portion of the oral treatment composition 131 may remain in the reservoir 111 and/or the delivery member 150, but a sufficient amount of the oral treatment composition 131 will be absorbed by the pad portion 210 of the applicator component 200.

In some embodiments, once the oral treatment composition 131 has been absorbed (entirely or mostly) by the liquid absorbing material of the pad portion 210 of the applicator component 200, the applicator component 200 may be placed into the user's oral cavity as described herein. Specifically, in some embodiments the applicator component 200 need not be detached from the storage and delivery component 100 to place the applicator component 200 within the oral cavity. Thus, the applicator component 200 could be placed into the user's oral cavity while it remains attached to the storage and delivery component 100. However, this may be a bulky endeavor and may prevent the user from adequately conforming the front surface 211 of the pad portion 210 of the applicator component 200 to the facial surfaces of the teeth, for example. That said, as mentioned herein above, in the exemplified embodiment the applicator component 200 is detachable from the storage and delivery component 100 and thus it may be so detached in order to apply or dispense the oral treatment composition 131 onto the user's teeth or other oral cavity surfaces. In some embodiments, the applicator component 200 may not be detachable from the storage and delivery component.

Figure 7:
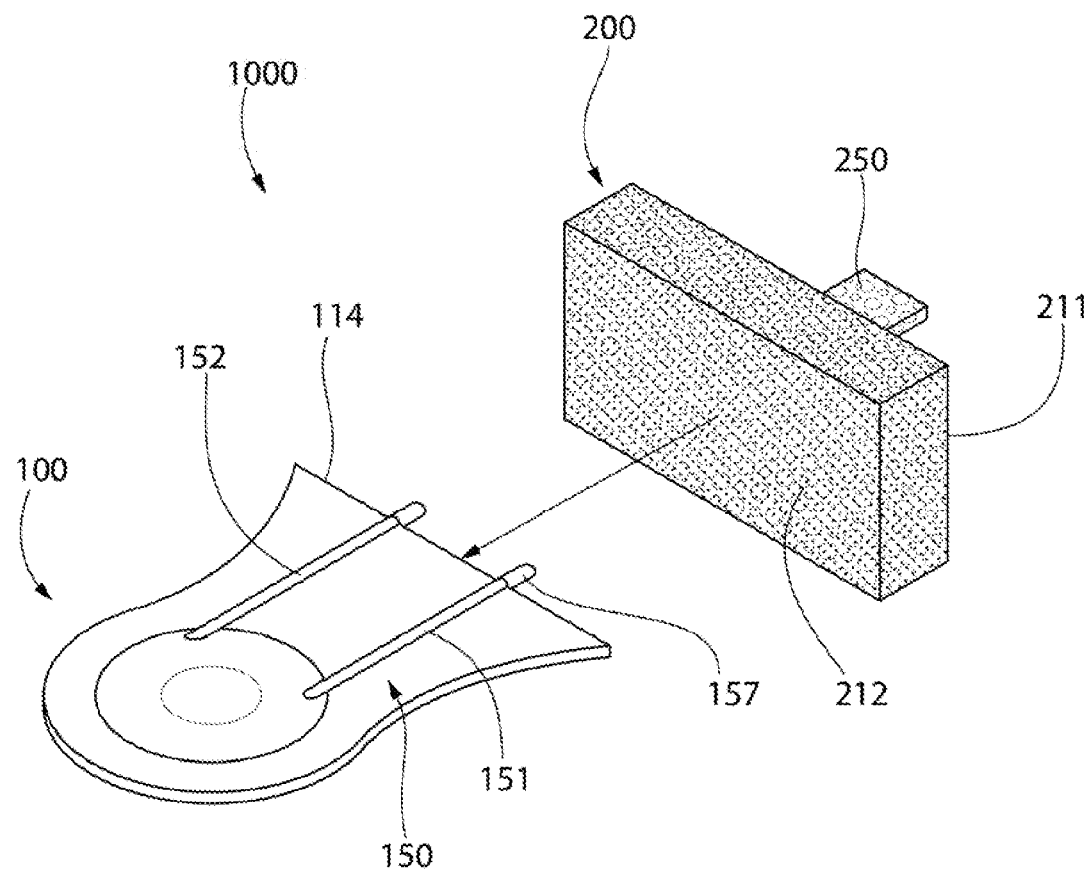
FIG. 7 is a perspective view of the oral treatment device of FIG. 1 illustrating the applicator component being detached from the storage and delivery component.

Referring to FIG. 7, the applicator component 200 is illustrated in a detached state whereby the applicator component 200 is detached from the storage and delivery component 100. To achieve the detached state, the applicator component 200 and the storage and delivery component 100 are simply pulled in opposing directions (or one of the applicator and storage and delivery components 100, 200 is pulled relative to the other) until the delivery member 150 (i.e., the first and second tubes 151, 152) are removed from the interior of the applicator component 200. As noted previously, the positioning of the first and second tubes 151, 152 within the applicator component 200 may be the only thing that couples the applicator component 200 to the storage and delivery component 100 in some embodiments. Thus, once the first and second tubes 151, 152 are removed and separated from the applicator component 200, the applicator component 200 is no longer attached in any way to the storage and delivery component 100.

With the applicator component 200 detached from the storage and delivery component 100, the portions of the first and second tubes 151, 152 that protrude from the end surface 114 of the body 110 become visible, as shown in FIG. 7. It is these portions of the first and second tubes 151, 152 (see, for example, the portion labeled 157) that facilitate the coupling between the applicator component 200 and the storage and delivery component 100 when those two components are attached.

Once the applicator component 200 is detached from the storage and delivery component 100, the applicator component 200 is ready to be placed inside of the user's oral cavity to provide a treatment thereto. No longer encumbered by the structure of the storage and delivery component 100, the applicator component 200 can now flex, bend, etc. to conform to whatever surface in the oral cavity it is intended to treat (such as, for example without limitation, the facial surfaces of the teeth). The applicator component 200 can be positioned entirely within the oral cavity in some embodiments.

Figure 8A:
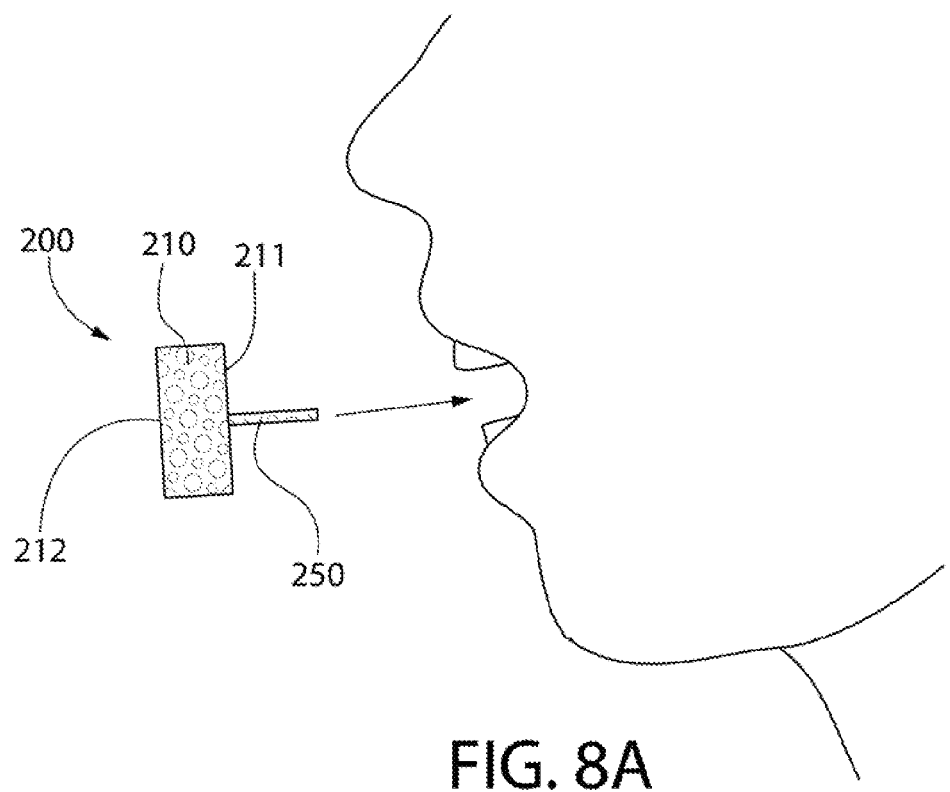
FIGS. 8A and 8B illustrate the applicator component being placed in contact with a user's teeth.
Figure 8B:
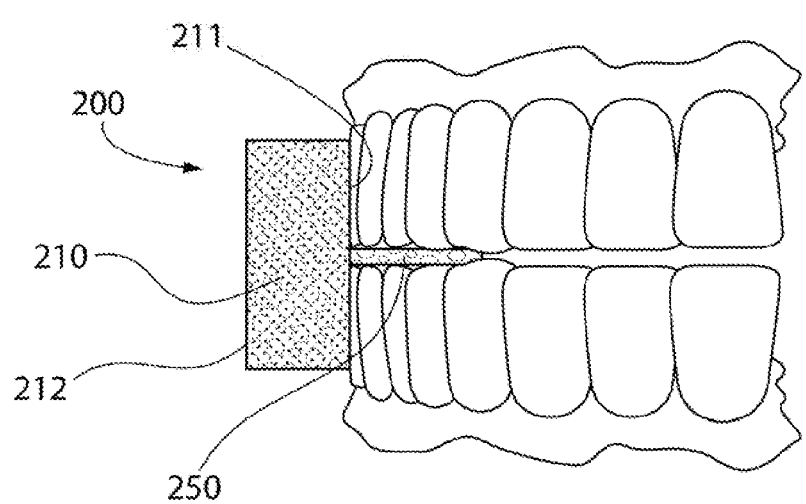

Referring to FIGS. 8A and 8B, placement of the applicator component 200 into the oral cavity of a user is depicted. In FIG. 8A, the user's mouth is open in anticipation of positioning of the applicator component 200 therein. The front surface 211 of the pad portion 210 of the applicator component 200 is facing the user's oral cavity. In this embodiment, the bite tab 250 protrudes from the front surface 211 of the pad portion 210 and is ready to be received in the space between the upper and lower teeth.

In FIG. 8B, the applicator component 200 has been placed into proper position within the oral cavity. The bite tab 250 is positioned between the occlusal surfaces of the upper and lower teeth so that the user can bite down on the bite tab 250 to hold the applicator component 200 in place. Of course, as mentioned above in other embodiments the bite tab 250 could be omitted and other techniques for holding the applicator component 200 in place may be used. For example, the applicator component 200 may have an adhesive surface that holds it in place, or the applicator component 200 may nest neatly in the space between the inner surface of the lip and the teeth, or the applicator component 200 may include features on its opposing lateral side surfaces that grab or otherwise interact with the back teeth to hold it in place. Basically, there are many ways to make sure that the applicator component 200 stays in position once placed inside the oral cavity.

As shown in FIG. 8B, in the exemplified embodiment the applicator component 200 is positioned so that the front surface 211 of the pad portion 210 of the applicator component 200 is in contact with facial surfaces of the user's teeth. Due to the pad portion 210 being formed of a liquid absorbing material, pressure applied onto the pad portion 210 due to it being squeezed between the lip and the teeth causes the oral treatment composition 131 held therein to dispense onto the facial surfaces of the teeth. Even if no such pressure is applied, there mere contact between the front surface 211 of the pad portion 210 of the applicator component 200 with the facial surfaces of the teeth will impart a benefit to the teeth, said benefit being dependent upon the particular type of composition being applied. Although in the exemplified embodiment the pad portion 210 contacts only the facial surfaces of the teeth, in other embodiments it could be bent and/or flexed to wrap around the teeth to cover the facial, occlusal, and/or distal surfaces of the teeth (or any one or two of those surfaces).

Figure 9:
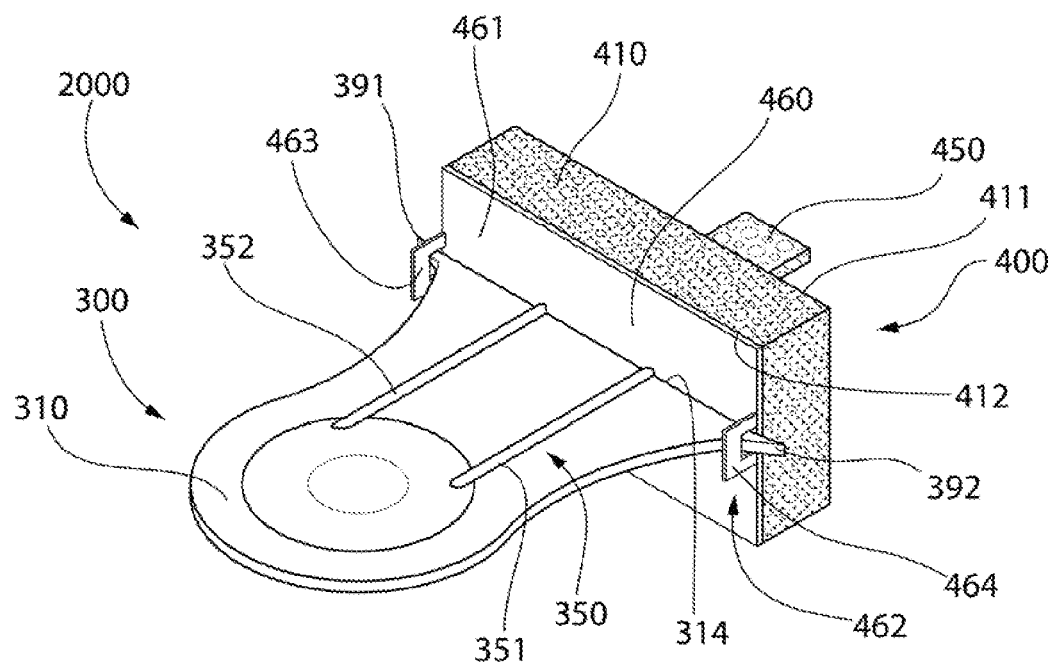
FIG. 9 is a perspective view of an oral treatment device in accordance with a second embodiment of the present invention, the oral treatment device including a storage and delivery component and an applicator component in an attached state.
Figure 10:
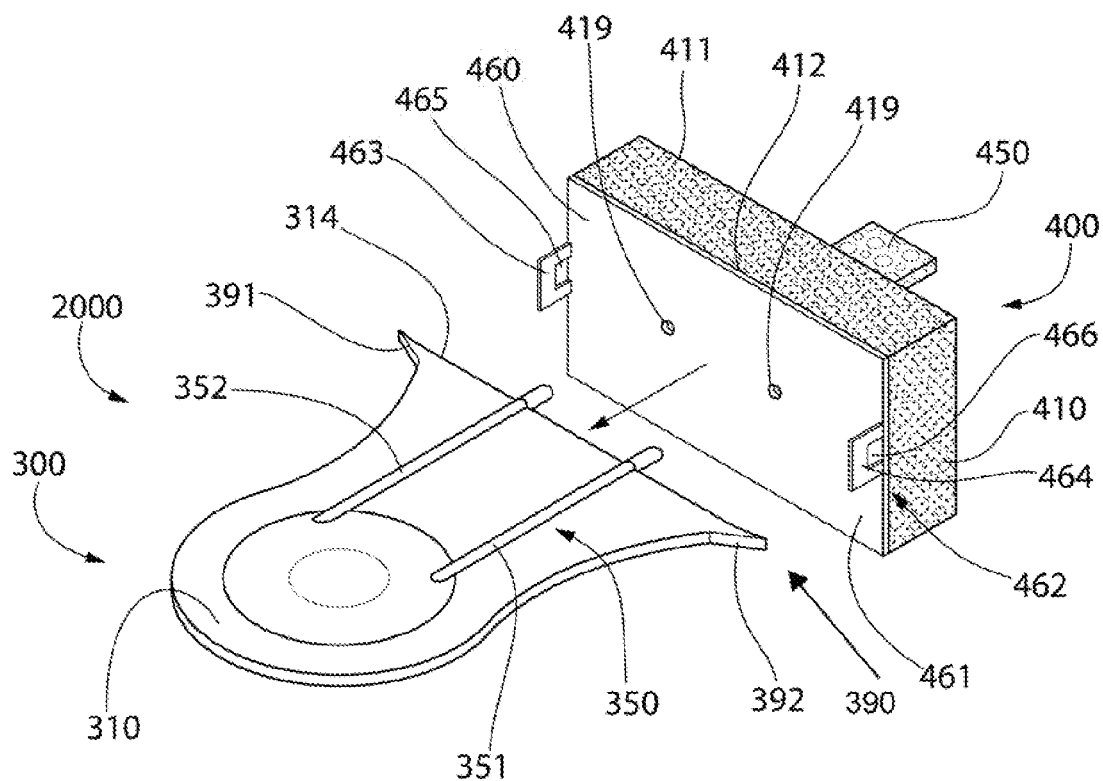
FIG. 10 is a perspective view of the oral treatment device of FIG. 9 illustrating the applicator component being detached from the storage and delivery component.

Referring now to FIGS. 9 and 10, an alternative embodiment of an oral treatment device 2000 will be described in accordance with an embodiment of the present invention. The oral treatment device 2000 comprises a storage and delivery component 300 and an applicator component 400 that are detachably coupled together. Specifically, in FIG. 9 the storage and delivery component 300 and the applicator component 400 are attached and in FIG. 10 the applicator component 400 has been detached from the storage and delivery component 300.

The storage and delivery component 300 is identical to the storage and delivery component 100 described above, except with regard to the differences described herein. Specifically, the storage and delivery component 300 comprises a body 310 that is identical to the body 110 of the storage and delivery component 100, except the body 310 of the storage and delivery component 300 comprises a connection element 390 for physically connecting the body 310 to the applicator component 400. In the exemplified embodiment, the connection element 390 comprises a first protrusion 391 and a second protrusion 392 protruding from opposite ends of the end surface 314 of the body 310. The first and second protrusions 391, 392 are configured to engage, mate with, or otherwise interact with a connection element of the applicator component 400 to facilitate coupling therebetween.

In that regard, in this embodiment the applicator component 400 comprises a pad portion 410 and a connection portion 460. The pad portion 410 comprises a front surface 411 and a rear surface 412, and there is a bite tab 450 protruding from the front surface 411. The connection portion 460 comprises a plate member 461 that is coupled to a rear surface 412 of the pad portion 410 and a connection element 462 protruding from the plate member 461. The connection portion 460 may be formed of a rigid material such as a hard plastic, metal, or the like in some embodiments, although the invention is not to be so limited in all embodiments.

There are a plurality of apertures 419 formed through the plate member 461 in the exemplified embodiment. These exist to enable the first and second tubes 351, 352 (the delivery members 350) to extend through the plate member 461 to contact the pad portion 410 of the applicator component 400 so that the oral treatment composition can flow to the pad portion 410 as described above.

In this embodiment, the connection element 462 comprises a first tab 463 extending from a first side of the plate member 461 and a second tab 464 extending from a second side of the plate member 461. In the exemplified embodiment, the first tab 463 comprises a first aperture 465 and the second tab 464 comprises a second aperture 466. When the applicator component 400 is coupled to the storage and delivery component 100, the protrusions 391, 392 of the body 310 of the storage and delivery component 300 nest within the apertures 465, 466 of the first and second tabs 463, 464, respectively, as shown in FIG. 9. This interaction physically couples the applicator component 400 to the storage and delivery component 300. Thus, when the applicator component 400 is attached to the storage and delivery component 300, the tubes 351, 352 extend through the apertures 419 so as to be fluidly coupled to the pad portion 410 and the first and second protrusions 391, 392 mate with the first and second tabs 463, 464 to create a physical coupling between the applicator component 400 and the body 310 of the storage and delivery component 300. To detach the applicator component 400 from the storage and delivery component 300, the first and second tabs 463, 464 may be flexed outwardly and then the applicator component 400 pulled away from the storage and delivery component 300 (pulling the applicator component 400 away from the storage and delivery component 300 may automatically detach the protrusions 391, 392 from the tabs 463, 464 in some embodiments).

Of course, various structures and/or techniques for coupling the applicator component 400 to the body 310 of the storage and delivery component 300 may be used in alternative embodiments. There may be straps, fasteners, various protrusions and mating recesses, or the like on either or both of the applicator component 400 and the storage and delivery component 300 to achieve the coupling therebetween. Thus, the invention is not to be limited by the particular structures used in FIGS. 9 and 10 for this purpose unless so specified in the claims.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral treatment device comprising:
   a storage and delivery component comprising:
     a body comprising a reservoir;
     an oral treatment composition in the reservoir;
     at least one delivery member extending from a first end to a second end, the first end being fluidly coupled to the reservoir; and a frangible barrier separating the oral treatment composition from the first end of the delivery member;
an applicator component comprising a pad portion formed of a liquid absorbing material, the applicator component alterable between: (1) an attached state whereby the second end of the delivery member is fluidly coupled to the pad portion; and (2) a detached state whereby the applicator component is detached from the storage and delivery component for application to a user's teeth;
wherein application of a force on the reservoir ruptures the frangible barrier to enable the oral treatment composition to flow through the at least one delivery member to the pad portion of the applicator component; and
wherein the body comprises an end surface, a portion of the at least one delivery member that comprises the second end protruding from the end surface, and wherein in the attached state the applicator component is adjacent to or in abutment with the end surface of the body and the portion of the at least one delivery member that protrudes from the end surface of the body is at least partially disposed within the pad portion of the applicator component.

2. The oral treatment device according to claim 1 wherein the frangible barrier comprises a capsule located in the reservoir, the oral treatment composition located in the capsule, and wherein application of the force on the reservoir alters the frangible capsule from a sealed state to an unsealed state to enable the oral treatment composition to flow through the at least one delivery member to the pad portion of the applicator component.

3. The oral treatment device according to claim 1 wherein the pad portion of the applicator component comprises a front surface and a rear surface, and wherein when the applicator component is in the attached state the second end of the delivery member is located within the liquid absorbing material of the pad portion between the front and rear surfaces of the pad portion.

4. The oral treatment device according to claim 1 wherein the at least one delivery member is a tube having a cross-sectional area that is configured to force the oral treatment composition to flow through the at least one delivery member by capillary action upon the frangible barrier being ruptured.

5. The oral treatment device according to claim 1 wherein the reservoir comprises an air gap that is free of the oral treatment composition when the frangible barrier is intact, and wherein the first end of the delivery member is located within the air gap of the reservoir.

6. The oral treatment device according to claim 1 wherein the pad portion of the applicator component comprises a front surface that is configured to contact facial surfaces of a user's teeth and a bite tab extending from the front surface.

7. The oral treatment device according to claim 1 wherein the applicator component comprises a front surface that is configured to contact the user's teeth and a rear surface opposite the front surface, the rear surface facing the storage and delivery component when the applicator component is in the attached state, and further comprising a liquid activated adhesive coating on the front surface of the applicator component to adhere the applicator component to the user's teeth during use.

8. The oral treatment device according to claim 1 wherein the applicator component comprises the pad portion and a connection portion, the connection portion comprising a connection element that is configured to interact with a connection element of the body of the storage and delivery component to mechanically couple the applicator component to the body of the storage and delivery component when in the attached state.

9. The oral treatment device according to claim 8 wherein the pad portion of the applicator component comprises a front surface and a rear surface, the connection portion comprising a plate member that is coupled to the rear surface of the pad portion, the connection element of the applicator component comprising a first tab extending from a first side edge of the plate and a second tab extending from a second side edge of the plate, the connection element of the body of the storage and delivery component comprising first and second protrusions, and wherein the first and second tabs comprise apertures that receive the first and second protrusions of the body of the storage and delivery component to mechanically couple the applicator component to the body of the storage and delivery component.

10. The oral treatment device according to claim 8 wherein the connection portion of the applicator component comprises at least one hole, and wherein a portion of the delivery member that comprises the second end extends through the at least one hole of the connection portion of the applicator component and into the pad portion of the applicator component.

11. The oral treatment device according to claim 1 wherein the applicator component is physically coupled to the at least one delivery member of the storage and delivery component and is not physically coupled to the body of the storage and delivery component.

12. The oral treatment device according to claim 1 wherein a portion of the delivery member that comprises the second end of the delivery member is embedded within the liquid absorbing material of the pad portion of the applicator component when the applicator component is in the attached state.

13. The oral treatment device according to claim 1 wherein the body of the storage and delivery component comprises a compressible portion that defines the reservoir, wherein application of the force on the compressible portion causes the compressible portion to compress, which in turn ruptures the frangible barrier so that the oral treatment composition can flow out of the reservoir and into the at least one delivery member.

14. The oral treatment device according to claim 1 wherein a first portion of the at least one delivery member is encapsulated within the body of the storage and delivery component and a second portion of the at least one delivery member protrudes from an edge of the body of the storage and delivery member, and wherein the second portion of the at least one delivery member is encapsulated within the applicator component so that no portion of the delivery member is exposed when the applicator component is in the attached state.

15. The oral treatment device according to claim 1 wherein the applicator component is pliable so that it can be flexed to conform to facial surfaces of the user's teeth.

16. The oral treatment device according to claim 1 wherein the pad portion of the applicator component comprises a front surface that is configured to contact the user's teeth during treatment, and wherein all exterior surfaces of the pad portion other than the front surface are coated with a waterproof coating so that the oral treatment composition is only dispensed from the front surface of the pad portion.

17. An oral treatment device comprising:
a storage and delivery component comprising:
a body comprising a reservoir;

an oral treatment composition in the reservoir;

a capillary member extending from a first end to a second end, the first end being fluidly coupled to the reservoir; and a frangible barrier separating the oral treatment composition from the first end of the capillary member; and an applicator component comprising a pad portion formed of a liquid absorbing material, the applicator component alterable between: (1) an attached state whereby the second end of the capillary member is in contact with the pad portion; and (2) a detached state whereby the applicator component is detached from the storage and delivery component for application to a user's teeth; and wherein the frangible barrier is alterable from a sealed state to an unsealed state, and wherein in the unsealed state the oral treatment composition flows from the reservoir to the pad portion of the applicator component through the capillary member due to capillary action.

18. The oral treatment device according to claim 17 wherein the capillary member comprises a tube having a cross-sectional area that is configured to force the oral treatment composition to flow through the tube naturally and passively due to capillary action.

19. An oral treatment device comprising:
a storage and delivery component comprising:
a body comprising a reservoir;
an oral treatment composition in the reservoir;
a capillary member extending from a first end to a second end, the first end being fluidly coupled to the reservoir; and
a frangible barrier separating the oral treatment composition from the first end of the capillary member; and an applicator component comprising a pad portion formed of a liquid absorbing material, wherein a portion of the capillary member that comprises the second end of the capillary member is embedded within the liquid absorbing material of the pad portion of the applicator component; and wherein upon rupture of the frangible barrier, the oral treatment composition flows from the reservoir to the pad portion of the applicator component through the capillary member due to capillary action.

* * * * *